United States Patent

Chassot et al.

(10) Patent No.: US 6,749,644 B2
(45) Date of Patent: Jun. 15, 2004

(54) 2-HYDROXY-5-AMINO-BIPHENYL-DERIVATIVES AND OXIDATIVE HAIR COLORING AGENTS CONTAINING SAID COMPOUNDS

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 180 days.

(21) Appl. No.: 10/049,346

(22) PCT Filed: Mar. 10, 2001

(86) PCT No.: PCT/EP01/02704

§ 371 (c)(1),
(2), (4) Date: Jan. 30, 2002

(87) PCT Pub. No.: WO02/02507

PCT Pub. Date: Jan. 10, 2002

(65) Prior Publication Data

US 2002/0166180 A1 Nov. 14, 2002

(30) Foreign Application Priority Data

Jul. 1, 2000 (DE) .......................... 100 32 134

(51) Int. Cl.$^7$ ................................. A61K 7/13
(52) U.S. Cl. .................. 8/405; 8/406; 8/421; 564/305; 564/306; 564/307; 564/308
(58) Field of Search ............... 8/405, 406, 421; 564/305, 306, 307, 308

(56) References Cited

U.S. PATENT DOCUMENTS

| 3,901,918 A | 8/1975 | Koga | 260/335 |
| 6,500,213 B1 * | 12/2002 | Braun et al. | 8/405 |

FOREIGN PATENT DOCUMENTS

| DE | 25 18 393 A | 11/1976 | |
| DE | 26 59 056 A | 7/1978 | |
| EP | 0 027 679 A | 4/1981 | |
| EP | 0 027 679 A2 * | 4/1981 | A61K/31/47 |
| EP | 0873 745 A2 | 10/1998 | |
| WO | WO 99/59527 * | 11/1999 | A61K/7/00 |

OTHER PUBLICATIONS

R.C. Weast: "CRC Handbook of Chemistry and Physics", 1988, CRC Press, US XP002176454 157200 Edition 69, p. C153.

Database Chemical Abstracts On Line! Access No. 113:23 572, XP002176455, Registry No. 127745–90–8 & A. Avdeenko: "Structure of Products in Reaction of N–Arenesulfonyl–P–Duinonimines with Naphthols", Zh. Org Khim., BD 25, Nr. 11, 1989, pp. 2375–2381.

Database Chemical Abstracts on Line, Access No. 77:61436, XP002176456, Registry No. 38045–22–6, & E. Titov et al: : Production of 2 . . . Khim. Tekhnol., Nr. 22, 1971, pp. 13–15, Kharkov.

68:104057 CA "Phenylphenol Derivatives with Biological Activity . . . " by Cheng et al., Agric. Biol. Chem. 1968, 32(3).

* cited by examiner

Primary Examiner—Brian P. Mruk
Assistant Examiner—Eisa Elhilo
(74) Attorney, Agent, or Firm—Michael J. Striker

(57) ABSTRACT

The object of the present invention are colorants for oxidative dyeing of keratin fibers, particularly hair, based on a developer-coupler combination containing as the developer at least one 2-hydroxy-5-amino-biphenyl derivative of general formula (I), and novel 2-hydroxy-5-aminobiphenyl derivatives.

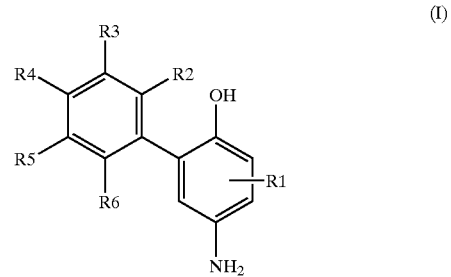

9 Claims, No Drawings

2-HYDROXY-5-AMINO-BIPHENYL-DERIVATIVES AND OXIDATIVE HAIR COLORING AGENTS CONTAINING SAID COMPOUNDS

The present invention relates to unsymmetrical 2-hydroxy-5-aminobiphenyl derivatives and to colorants for oxidative dyeing of keratin fibers, particularly human hair, based on a developer/coupler combination containing a 2-hydroxy-5-aminobiphenyl derivative as the developer.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, p-phenylenediamines and p-aminophenol, and suitable couplers are, for example, resorcinols, 1-naphthol, 3-aminophenols and m-phenylenediamine.

The oxidation dyes used for dyeing human hair must meet numerous requirements in addition to that of being able to produce colorations of the desired intensity. For example, these dyes must be harmless from a toxicological and dermatological standpoint, and the obtained hair colorations must have good light fastness, resistance to permanent waving, acid fastness and rubbing fastness. In any case, however, such colorations must remain stable over a period of at least 4 to 6 weeks in the absence of exposure to light, rubbing and chemical agents. Moreover, by combination of appropriate developers and couplers, it must be possible to create a wide range of different color shades.

The use of certain symmetrical diaminodihydroxydiphenyls in oxidative hair colorants is known from German Unexamined Patent Application [DE-OS] 25 18 393. These colorants, however, produce only olive-brown to green-gray colorations. Hence, a need continued to exist for novel developers capable of producing a broader range of color shades.

We have now found that blond to red shades can be obtained by coupling a 2-hydroxy-5-aminobiphenyl derivative of general formula (I) with a common coupler.

Hence, the object of the present invention is a colorant for oxidative dyeing of keratin fibers, for example wool, furs, feathers or hair, particularly human hair, based on a developer-coupler combination containing as the developer a 2-hydroxy-5-aminobiphenyl derivative of general formula (I) or a physiologically tolerated water-soluble salt thereof

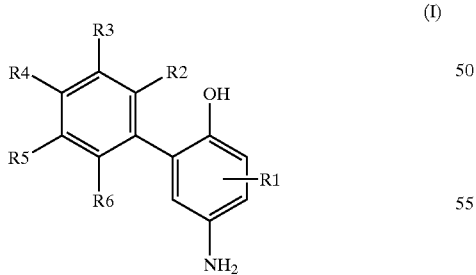

(I)

wherein
R1 denotes hydrogen, a halogen atom, $C_1$–$C_4$-alkyl group a $C_1$–$C_4$-hydroxyalkyl group, $C_1$–$C_4$-alkoxy group or a $C_1$–$C_4$-hydroxyalkoxy group;
R2, R3, R4, R5, R6 can be equal or different and independently of each other denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group ($NH_2$), an alkylamino group, a dialkylamino group, a trifluoromethyl group, a —C(O)H group, a —C(O)$CH_3$ group, a —C(O)$CF_3$ group, an —Si($CH_3$)$_3$ group, a $C_1$–$C_4$-hydroxyalkyl group, a $C_3$–$C_4$-dihydroxyalkyl group, a —CH=CHR7 group, a —($CH_2$)$_p$—$CO_2$R8 group or a —($CH_2$)$_p$R9 group, with p=1,2,3 or 4, a —C(R10)=NR11 group, or a C(R12)H—NR13R14 group, or two adjacent R2 to R6 groups form an —O—$CH_2$—O— bridge;
R7 denotes hydrogen, a hydroxyl group, a nitro group, an amino group, a —$CO_2$R12 group or a —C(O))$CH_3$ group;
R8, R10 and R13 can be equal or different and independently of each other denote hydrogen or a $C_1$–$C_4$-alkyl group;
R9 denotes an amino group or a nitrile group;
R11, R14 and R15 can be equal or different and independently of each other denote hydrogen, a hydroxyl group, a $C_1$–$C_4$-alkyl group, a $C_1$–$C_4$-hydroxyalkyl group, a $C_3$–$C_4$-dihydroxyalkyl group or a radical of formula

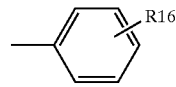

R12 denotes hydrogen, an amino group or a hydroxyl group, provided that the compound of formula (I) does not present a center of symmetry.

Suitable compounds of formula (I) are, for example:
2-hydroxy-3-chloro-5-aminobiphenyl; 2-hydroxy-3-methyl-5-aminobiphenyl; 2-hydroxy-4-chloro-5-aminobiphenyl; 2-hydroxy-4-methyl-5-aminobiphenyl; 2,2'-dihydroxy-5-aminobiphenyl; 2,3'-dihydroxy-5-aminobiphenyl; 2,4'-dihydroxy-5-aminobiphenyl; 2,5'-dihydroxy-5-aminobiphenyl; 2,6'-dihydroxy-5-aminobiphenyl; 2-hydroxy-5,2'-diaminobiphenyl; 2-hydroxy-5,3'-diaminobiphenyl; 2-hydroxy-5,4'-diaminobiphenyl; 2-hydroxy-5,5'-diaminobiphenyl; 2-hydroxy-5,6'-diaminobiphenyl; 2,2',3'-trihydroxy-5-aminobiphenyl; 2,2',4'-trihydroxy-5-aminobiphenyl; 2,2',5'-trihydroxy-5-aminobiphenyl; 2,2',6'-trihydroxy-5-aminobiphenyl; 2,3',4'-trihydroxy-5-aminobiphenyl; 2,3',5'-trihydroxy-5-aminobiphenyl; 2-hydroxy-5,2',3'-triaminobiphenyl; 2-hydroxy-5,2',4'-triaminobiphenyl; 2-hydroxy-5,2',5'-triaminobiphenyl; 2-hydroxy-5,2',6'-triaminobiphenyl; 2-hydroxy-5,3',4'-triaminobiphenyl; 2-hydroxy-5,3',5'-triaminobiphenyl; 2-hydroxy-5,3',4'-triaminobiphenyl; 2-hydroxy-5,3',5'-triaminobiphenyl, 2,2'-dihydroxy-5,3'-diaminobiphenyl; 2,2'-dihydroxy-5,4'-diaminobiphenyl; 2,2'-dihydroxy-5,6'-diaminobiphenyl; 2,3'-dihydroxy-5,4'-diaminobiphenyl; 2,3'-dihydroxy-5,5'-diaminobiphenyl; 2,3'-dihydroxy-5,6'-diaminobiphenyl; 2-hydroxy-5-amino-2'-aminomethylbiphenyl; 2-hydroxy-5-amino-2'-chlorobiphenyl; 2-hydroxy-5-amino-2'-cyano biphenyl; 2-hydroxy-5-amino-2'-fluorobiphenyl; 2-hydroxy-5-2'-methoxybiphenyl; 2-hydroxy-5-amino-2'-methylbiphenyl; 2-hydroxy-5-amino-2'-methylsulfanylbiphenyl; 2-hydroxy-5-amino-2'-nitrobiphenyl; 2-hydroxy-5-amino-3'-aminomethylbiphenyl; 2-hydroxy-5-amino-3'- chlorobiphenyl; 2-hydroxy-5-amino-3'-cyanobiphenyl; 2-hydroxy-5-amino-3'-flurobiphenyl; 2-hydroxy-5-amino-3'-methoxybiphenyl; 2-hydroxy-5-amino-3'-methylbiphenyl; 2-hydroxy-5-amino-3'-methylsulfanylbiphenyl; 2-hydroxy-5-amino-3'-nitrobiphenyl; 2-hydroxy-5-amino-4'-aminomethylbiphenyl; 2-hydroxy-5-amino-4'-chlorobiphenyl; 2-hydroxy-5-amino-4'-cyanobiphenyl; 2-hydroxy-5-amino-4'-fluorobiphenyl; 2-hydroxy-5-amino-4'-methoxybiphenyl; 2-hydroxy-5-amino-4'-methylbiphenyl; 2-hydroxy-5-amino-4'-methylsulfanylbiphenyl; 2-hydroxy-5-amino-4'-nitrobiphenyl; 2-hydroxy-5-amino-5'-aminomethylbiphenyl; 2-hydroxy-5-amino-5'-chlorobiphenyl; 2-hydroxy-5-amino-5'-cyanobiphenyl; 2-hydroxy-5-amino-5'-fluorobiphenyl; 2-hydroxy-5-amino-5'-methoxybiphenyl; 2-hydroxy-5-amino-5'-methyl-biphenyl; 2-hydroxy-5-amino-5'-methylsulfanybiphenyl; 2-hydroxy-5-amino-5'-nitrobiphenyl; 2-hydroxy-5-amino-6'-amino-methylbiphenyl; 2-hydroxy-5-amino-6'-chlorobiphenyl; 2-hydroxy-5-amino-6'-cyanobiphenyl; 2-hydroxy-5-amino-6'-fluorobiphenyl; 2-hydroxy-5-amino-6'-methoxybiphenyl; 2-hydroxy-5-amino-6'-methylbiphenyl; 2-hydroxy-5-amino-6'-methylsulfanylbiphenyl; 2-hydroxy-5-amino-6'-nitrobiphenyl; 2,2'-dihydroxy-5-amino-3'-methylbiphenyl; 2,2'-dihydroxy-5-amino-4'-methylbiphenyl; 2,2'-dihydroxy-5-amino-5'-methylbiphenyl; 2,2'-dihydroxy-5-amino-6'-methylbiphenyl; 2,3'-dihydroxy-5-amino-4'-methylbiphenyl; 2,3'-dihydroxy-5-amino-5'-methylbiphenyl; 2-hydroxy-5-amino-2',3'-dimethoxybiphenyl; 2-hydroxy-5-amino-2',3-dimethylbiphenyl; 2-hydroxy-5-amino-2',4'-dimethoxybiphenyl; 2-hydroxy-5-amino-2',4'-dimethylbiphenyl; 2-hydroxy-5-amino-2',5'-dimethoxybiphenyl; 2-hydroxy-5-amino-2',5'-dimethylbiphenyl; 2-hydroxy-5-amino-2',6'-dimethoxybiphenyl; 2-hydroxy-5-amino-2',6'-dimethylbiphenyl; 2-hydroxy-5-amino-3',4'-dimethoxybiphenyl; 2-hydroxy-5-amino-3',4'-dimethylbiphenyl; 2-hydroxy-5-amino-3',5'-dimethoxybiphenyl; 2-hydroxy-5-amino-3',5'-dimethylbiphenyl; 2-hydroxy-5-amino-2'-methoxy-3'-methylbiphenyl; 2-hydroxy-5-amino-2'-methoxy-4'-methylbiphenyl; 2-hydroxy-5-amino-2'-methoxy-5'-methylbiphenyl; 2-hydroxy-5-amino-2'-methoxy-6'-methylbiphenyl; 2-hydroxy-5-amino-3'-methoxy-4'-methylbiphenyl; 2-hydroxy-5-amino-3'-methoxy-5'-methylbiphenyl; 4-amino-2-benzo-[1,3]dioxol-5-ylphenol; 4-amino-2-benzo[2,4]dioxol-5-ylphenol and 2-hydroxy-5-amino-4'-(2-hydroxyethoxy)biphenyl.

Particularly preferred are compounds of formula (I) wherein (i) R1 denotes hydrogen or (ii) four of the R2 to R6 groups denote hydrogen while the fifth group denotes hydrogen, a methyl group, an amino group, a hydroxyl group, a $C_1$–$C_4$-hydroxyalkyl group or a methoxy group, or (iii) the groups R1 to R6 at the same time denote hydrogen, or (iv) R1 denotes hydrogen and four of the R2 to R6 groups denote hydrogen while the fifth group denotes hydrogen, a methyl group, an amino group, a hydroxyl group, a $C_1$–$C_4$-hydroxyalkyl group or a methoxy group.

Outstandingly suitable 2-hydroxy-5-aminobiphenyl derivatives of formula (I) in terms of the overall invention are 2-hydroxy-5-aminobiphenyl; 2,4'-dihydroxy-5-aminobiphenyl, 2-hydroxy-5-amino-4'-(2"-hydroxyethoxy) biphenyl, 2,4'-dihydroxy-5-amino-2'-methylbiphenyl, 2-hydroxy-5-amino-4'-(2"-hydroxyethyl)biphenyl, 2-hydroxy-5,4'-diaminobiphenyl or physiologically tolerated salts thereof.

The compounds of formula (I) can be used either as free bases or in the form of their physiologically tolerated salts with inorganic or organic acids, for example hydrochloric acid, sulfuric acid, phosphoric acid, acetic acid, propionic acid, lactic acid or citric acid.

The 2-hydroxy-5-aminobiphenyl derivative of formula (I) is contained in the colorant of the invention in an amount from about 0.005 to 20 wt. %, an amount from about 0.01 to 5.0 wt. % and particularly from 0.1 to 2.5 wt. % being especially preferred.

Preferred couplers are 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl) amino]-1,5-dimethoxybenzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di-(2-hydroxyethyl)amino]-aniline, 4-amino-2-di-[(2-hydroxyethyl)amino]-1-ethoxybenzene,5-methyl-2-(1-methylethyl)phenol, 3-[(2-hydroxyethyl)amino]aniline,3-[(2-aminoethyl)amino]aniline, 1,3-di-(2,4-diaminophenoxy) propane,di-(2,4-diaminophenoxy)methane, 1,3-diamino-2,4-dimethoxybenzene, 2,6-bis-(2-hydroxyethyl) aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(2-hydroxyphenyl)amino]acetamide, 5-[(2-hydroxyethyl)amino]-2-methylphenol, 3-[(2-hydroxyethyl)amino]phenol, 3-[(2-methoxyethyl)amino] phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although the advantageous properties of the 2-hydroxy-5-aminobiphenyl derivatives of formula (I) described here suggest that said derivatives should be used as the only developers, it is, of course, also possible to use the 2-hydroxy-5-aminobiphenyl derivatives of formula (I)

together with known developers such as, for example, 1,4-diaminobenzene, 2,5-diaminotoluene, 2,5-diaminophenylethyl alcohol, 4-aminophenol and the derivatives thereof, for example 4-amino-3-methylphenol, 4,5-diaminopyrazole derivatives, for example 4,5-diamino-1-(2-hydroxyethyl)pyrazole, or tetraaminopyrimidines.

The couplers and developers can be contained in the colorants of the invention either alone or in admixture with each other, the total amount of couplers and developers in the colorants of the invention (based on the total amount of colorant) being in all cases from about 0.005 to 20 wt. %, preferably from about 0.01 to 5.0 wt. % and particularly from 0.1 to 2.5 wt. %.

The total amount of developer-coupler combination contained in the colorants described herein is preferably from about 0.01 to 20 wt. %, an amount from about 0.02 to 10 wt. % and particularly from 0.2 to 6.0 wt. % being especially preferred. In general, the developers and couplers are used in approximately equimolar amounts. It is not disadvantageous in this respect, however, if the developers are present in a certain excess or deficiency (for example in a coupler: developer ratio from 1:2 to 1:0.5.

Moreover, the colorants of the invention can additionally contain other components, for example 6-amino-2-methylphenol and 2-amino-5-methylphenol, as well as other common direct dyes from the group consisting of acid and basic dyes, triphenylmethane dyes, anthraquinone dyes, aromatic nitro dyes, azo dyes, food dyes or disperse dyes.

The colorants can contain these dye components in an amount from about 0.1 to 4.0 wt. %.

Naturally, the couplers and developers and the other dye components, as long as they are bases, can also be used in the form of physiologically tolerated salts of organic or inorganic acids, for example hydrochloric acid or sulfuric acid or—providing that they contain aromatic OH groups—in the form of salts of bases, for example as alkali metal phenoxides.

Moreover, if the colorants are to be used for coloring hair, they can contain other common cosmetic additives, for example antioxidants such as ascorbic acid, thioglycolic acid or sodium sulfite, as well as perfume oils, complexing agents, wetting agents, emulsifiers, UV absorbers, thickeners and hair-care agents. The colorant of the invention can be a solution, particularly an aqueous or aqueous-alcoholic solution. A particularly preferred formulation form, however, is a cream, gel or emulsion. Such a composition consists of a mixture of the dye components and the usual additives employed for such preparations.

Common additives to solutions, creams, emulsions or gels are, for example, solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5.0 wt. %.

Depending on the composition, the colorants of the invention can be weakly acidic, neutral or alkaline. In particular, they have a pH of about 6.5 to 11.5. Adjustment to a basic pH is preferably done with ammonia, but it can also be done with an organic amine, for example monoethanolamine or triethanolamine, or with an inorganic base such as sodium hydroxide or potassium hydroxide. Suitable for adjustment to an acidic pH are inorganic or organic acids, for example phosphoric acid, acetic acid, citric acid or tartaric acid.

For oxidative dyeing of hair, the afore-described colorants are mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its compounds of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 2-hydroxy-5-aminobiphenyl derivative of formula (I) give hair colorations of excellent color fastness, particularly in terms of light fastness, wash fastness and rubbing fastness. As far as the dyeing properties are concerned, the hair colorants of the invention provide a wide range of different color shades from blond to brown, purple, violet and even blue and black, depending on the type and composition of the dye components. Such color shades are characterized by unusual color intensity. The very good coloring properties of the colorant of the present invention also manifest themselves in that these colorants make it possible to dye graying hair, chemically not previously damaged, without any problems and with good covering power. The 2-hydroxy-5-aminobiphenyl derivatives of formula (I) are water-soluble and give colorations of high intensity and excellent color fastness, particularly in terms of light fastness, wash fastness and rubbing fastness. They also have excellent storage stability, particularly as components of the aforedescribed colorants.

Another object of the present invention are novel 2-hydroxy-5-aminobiphenyl derivatives of formula (Ia) or physiologically tolerated, water-soluble salts thereof

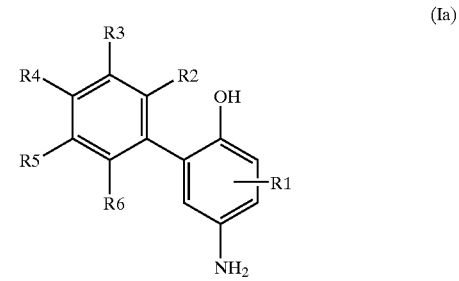

wherein
R1 denotes hydrogen, a halogen atom, a $C_1$–$C_4$-alkyl group, a $C_1$–$C_4$-hydroxyalkyl group, a $C_1$–$C_4$-alkoxy group or a $C_1$–$C_4$-hydroxyalkoxy group;

R2, R3, R4, R5, R6 can be equal or different and independently of each other denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a dialkylamino group, a trifluoromethyl group, a —C(O)H group, a —C(O)CH$_3$ group, a —C(O)CF$_3$ group, an —Si(CH$_3$)$_3$ group a $C_1$–$C_4$-hydroxyalkyl group, a $C_3$–$C_4$-dihydroxyalkyl group, a —CH=CHR7 group, a —(CH$_2$)$_p$—CO$_2$R8 group or a —(CH$_2$)$_p$—R9 group with p=1,2,3 or 4, a —C(R10)=NR11 group or a C(R12)H—NR13R14 group, or two adjacent R2 to R6 groups form an —O—CH$_2$—O— bridge;

R7 denotes hydrogen, a hydroxyl group, a nitro group, an amino group, a CO$_2$R12 group, or a —C(O)CH$_3$ group;

R8, R10 and R13 can be equal or different and independently of each other denote hydrogen or a $C_1$–$C_4$-alkyl group;

R9 denotes an amino or nitrile group;

R11, R14 and R15 can be equal or different and independently of each other denote hydrogen, a hydroxyl group, a $C_1$–$C_4$-alkyl group, a $C_1$–$C_4$-hydroxyalkyl group, a $C_3$–$C_4$-dihydroxyalkyl group or a radical of formula

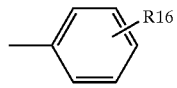

R12 denotes hydrogen, an amino group or a hydroxyl group, provided that the compound of formula (I) has no center of symmetry and that group R2 does not denote hydrogen or a hydroxyl group.

The 2-hydroxy-5-aminobiphenyl derivatives of formula (I) can be prepared by use of known methods of synthesis, for example methods similar to the general methods described in the following preparative examples.

The following examples illustrate the invention in greater detail without limiting its scope.

EXAMPLES

Example 1

Synthesis of 2-hydroxy-5-aminobiphenyl Hydrochloride

A. Synthesis of 2-Bromo-4-nitrophenol

2-Bromo-4-nitrophenol was prepared by reaction of 4-nitrophenol and N-bromosuccinimide. The experimental method of preparation was described by T. Oberhouser in J. Org. Chem. 1997 (62), page 4504.

B. Synthesis of 2-Bromo-1-methoxymethoxy-4-nitrobenzene

A total of 4.2 g (140 mmoles) of a sodium hydride dispersion (55% in oil) was added portionwise to a solution of 15.3 g (70.0 mmoles) of 2-bromo-4-nitrophenol from step A in 250 mL of tetrahydrofuran (THF) at 0° C. The reaction mixture was then allowed to agitate 50 min at 0° C. after which 1.83 g (19.4 mmoles) of chloromethyl methyl ether was added. The mixture was allowed to agitate for an additional hour at 0° C. after which it was worked up. To this end, the reaction mixture was poured onto ice and extracted with ethyl acetate. The organic phase was washed with a saturated aqueous solution of sodium chloride, dried over sodium sulfate, filtered and concentrated.

The residue was purified on silica gel using petroleum ether/ethyl acetate (9:1) [as eluent].

This gave 15.8 g (80% of the theoretical) of 2-bromo-1-methoxymethoxy-4-nitrobenzene.

$^1$H-NMR (300 MHz, CDCl$_3$): δ=8.48 (s, 1H); 7.08 (d,1H); 8.16 (d, 1H); 7.26 (d, 1H); 5.36 (s, 2H); 3.53 (s, 3H).

C. Synthesis of 2-Hydroxy-5-nitrobiphenyl 5.3 g (0.02 mole) of 2-bromo-1-methoxymethoxy-4-nitrobenzene from step B and 2.80 g (0.023 mole) of phenylboric acid were dissolved in 70 mL of 1,2-dimethoxyethane under argon. Then, 0.5 g (0.0005 mole) of tetrakis-(triphenylphosphine)palladium and 13 mL of 2 N potassium carbonate solution were added, and the reaction mixture was heated to 80° C. At the end of the reaction, the reaction mixture was poured into 100 mL of ethyl acetate and the organic phase was extracted with dilute sodium hydroxide solution and then dried with magnesium sulfate. The solvent was distilled off in a rotary evaporator, and the residue was purified on silica gel using petroleum ether/ethyl acetate (9:1). The product thus obtained was heated to 50° C. in a mixture of 40 mL of ethanol and 15 mL of a 2.9 M ethanolic hydrochloric acid solution. After neutralization with NaOH, the solvent was distilled off in a rotary evaporator, and the residue was purified by vacuum distillation. This gave 3.5 g (82% of the theoretical) of 2-hydroxy-5-nitrobiphenyl.

$^1$H-NMR (300 MHz, CDCl$_3$): δ=8.2 (m, 2H), 7.55 (m, 2H), 7.49 (m, 3H), 7.08 (d, 1H), 6.14 (s, 1H).

D. Synthesis of 2-Hydroxy-5-aminobiphenyl Hydrochloride 2.9 g (13.5 mmoles) of 2-hydroxy-5-nitrobiphenyl from step C was dissolved in 40 mL of ethanol and hydrogenated in the presence of 600 mg of palladium—active carbon catalyst (10%) at 25° C. After the theoretically required amount of hydrogen had been absorbed, the catalyst was filtered off. The solution was concentrated in a rotary evaporator. The phenol was then purified by vacuum distillation and to it was added 2.9 M ethanolic hydrochloric acid solution. The precipitated product was filtered off and dried.

This gave 0.5 g (17% of the theoretical) of 2-hydroxy-5-aminobiphenyl [Sic—The hydrochloride seems to be meant—Translator] with a melting point of 130–132° C.

| CHN Analysis (C$_{12}$H$_{12}$NOCl) | | | |
|---|---|---|---|
| | % C | % H | % N |
| Calculated | 65.02 | 5.46 | 6.32 |
| Found | 62.28 | 5.45 | 6.05 |

Example 2

Synthesis of Substituted 2-Hydroxy-5-aminobiphenyl Derivatives of General Formula (I) (General Method of Synthesis)

A. Synthesis of tert.Butyl N-(3-bromo-4-hydroxyphenyl) carbamate

A solution of 9.4 g (52.8 mmoles) of N-bromosuccinimide in 450 mL of chloroform was added dropwise to a suspension 10 g (47.8 mmoles) of tert.butyl N-(4-hydroxy-phenyl) carbamate in 100 mL of chloroform at 0° C. over a period of 2 hours. The reaction mixture was stirred for an additional 15 min and then washed twice with water (first with 400 mL, then with 200 mL), dried over magnesium sulfate, filtered and partly evaporated. Hexane was added to the residue with stirring which caused the formation of a precipitate. The precipitate was filtered off and washed with hexane.

This gave 9.7 g (70% of the theoretical) of tert.butyl N-(3-bromo-4-hydroxyphenyl) carbamate.

$^1$H-NMR (300 MHz, CDCl$_3$): δ=7.68 (br s, 1H); 7.05 (dd, 1H); 6.93 (d, 1H); 6.37 (br s; 2H); 5.39 (s, 1 H); 1.51 (s, 9H).

B. Synthesis of tert.Butyl N-(3-Bromo-4-ethoxymethoxyphenyl)carbamate 0.76 g (17.4 mmoles) of a sodium hydride dispersion (55% in oil) was added portionwise at 0° C. to a solution of 5 g (17.4 mmoles) of tert.butyl N-(3-bromo-4-hydroxyphenyl)carbamate from step A in 60 mL of THF. The mixture was then stirred for 50 min at 0° C. after which 1.83 g (19.4 mmoles) of chloromethyl ethyl ether was added. The mixture was stirred for an hour at 0° C. It was then poured onto ice and extracted with ethyl acetate, and the organic phase was washed with a saturated aqueous sodium chloride solution, dried over Na$_2$SO$_4$, filtered and concentrated. The residue was purified on silica gel with petroleum ether/ethyl acetate (9:1).

This gave 4.8 g (80% of the theoretical) of tert.butyl N-(3-bromo-4-hydroxyphenyl)-carbamate.

$^1$H-NMR (300 MHz, CDCl$_3$): δ=7.66 (d, 1H); 7.16 (dd, 1H); 7.08 (d, 1H); 5.23 (s, 2H); 3.77 (q, 2H); 1.51 (s, 9H); 1.22 (t, 3H).

C. Synthesis of tert.Butyl N-{4-ethoxymethoxy-3-(4,4,5,5-tetramethyl[1,3,2]dioxaborolan-2-yl)phenyl}carbamate 210 mL of degassed dioxane was added under argon to a mixture of 7.0 g (20.2 mmoles) of tert.butyl N-(3-bromo-4-ethoxymethoxyphenyl)carbamate from step B, 12.8 g (50.6 mmoles) of diboronpinacol ester, 2.0 g (2.9 mmoles) of dichloro-1,1'-bis-[diphenylphosphino)ferrocene]palladium [PdCl$_2$(dppf)] and 6.2 g (63.2 mmoles) of potassium acetate. The mixture was stirred 26 hours at 80° C. after which to it was added a mixture of 4.2 g (16.9 mmoles) of diboronpinacol ester and 700 mg (0.95 added a mixture of 4.2 g (16.9 mmoles) of diboronpinacol ester and 700 mg (0.95 mmole) of PdCl$_2$(dppf). The reaction mixture was stirred at 80° C. for an additional 14 hours. The reaction mixture was then poured into water and extracted with ethyl acetate, and the organic phase was washed with a saturated aqueous sodium chloride solution, dried over sodium sulfate, filtered and concentrated. The resulting crude product was purified on deactivated silica gel with hexane/ethyl acetate (1:1).

This gave 5.30 g (61% of the theoretical) of tert.butyl N-{4-ethoxymethoxy-3-(4,4,5,5-tetramethyl-[1,3,2]dioxaborolan-2-yl)phenyl}carbamate.

D. Synthesis of Substituted 2-Hydroxy-5-aminobiphenyl Derivatives 0.036 g (0.0001 mole) of tert.butyl N-[4-ethoxymethoxy-3-(4,4,5,5-tetramethyl-[1,3,2]dioxaborolan-2-yl)phenyl] carbamate from step C and 0.013 mole of the corresponding bromo derivative were dissolved in 70 mL of 1,2-dimethoxyethane under argon. Then, 0.5 g (0.0005 mole) of tetrakis-(triphenylphosphine)palladium and 13 mL of a 2 N potassium carbonate solution were added, and the reaction mixture was heated to 80° C. At the end of the reaction, the reaction mixture was poured into 100 mL of ethyl acetate, and the organic phase was extracted with dilute sodium hydroxide solution and then dried over magnesium sulfate. The solvent was distilled off under vacuum in a rotary evaporator, and the residue was purified on silica gel using petroleum ether/ethyl acetate (9:1). The resulting product in 40 mL of ethanol was heated to 50° C. To prepare the hydrochloride, 15 ml of a 2.9 M ethanolic hydrochloric acid solution was then added dropwise. The precipitate was filtered off, washed twice with 10-mL portions of ethanol and dried.

2.1 2-Hydroxy-5-amino-2'-methylbiphenyl Hydrochloride

| Bromo derivative used: | 2-bromotoluene |
|---|---|
| Yield: | 95% of the theoretical |
| Mass spectrum: | MH$^+$ 199 (100) |

2.2 2-Hydroxy-5-amino-3'-methylbiphenyl Hydrochloride

| Bromo derivative used: | 3-bromotoluene |
|---|---|
| Yield: | 84% of the theoretical |
| Mass spectrum: | MH$^+$ 199 (100) |

2.3 2-Hydroxy-5-amino-4'-methylbiphenyl Hydrochloride

| Bromo derivative used: | 4-bromotoluene |
|---|---|
| Yield: | 88% of the theoretical |
| Mass spectrum: | MH$^+$ 199 (100) |

2.4 2-Hydroxy-5,4'diaminobiphenyl Hydrochloride

| Bromo derivative used: | 4-bromoaniline |
|---|---|
| Yield: | 91% of the theoretical |
| Mass spectrum: | MH$^+$ 237 (100) |

2.5 5-Aminobiphenyl-2,4'-diol Hydrochloride

| Bromo derivative used: | 4-bromophenol |
|---|---|
| Yield: | 96% of the theoretical |
| Mass spectrum: | MH$^+$ 201 (100) |

2.6 5-Aminobiphenyl-2,3'-diol Hydrochloride

| Bromo derivative used: | 3-bromophenol |
|---|---|
| Yield: | 95% of the theoretical |
| Mass spectrum: | MH$^+$ 201 (100) |

2.7 2-Hydroxy-5-amino-4'-fluorobiphenyl Hydrochloride

| Bromo derivative used: | 1-bromo-4-fluorobenzene |
|---|---|
| Yield: | 95% of the theoretical |
| Mass spectrum: | MH$^+$ 203 (100) |

2.8 2-Hydroxy-5-amino-2'-fluorobiphenyl Hydrochloride

| Bromo derivative used: | 1-bromo-2-fluorobenzene |
|---|---|
| Yield: | 95% of the theoretical |
| Mass spectrum: | MH$^+$ 203 (100) |

2.9 5'-Amino-2'-hydroxybiphenyl-4-carbonitrile Hydrochloride

| | |
|---|---|
| Bromo derivative used: | 4-bromobenzonitrile |
| Yield: | 95% of the theoretical |
| Mass spectrum: | MH$^+$ 210 (100) |

2.10 5'-Amino-2'-hydroxybiphenyl-3-carbonitrile Hydrochloride

| | |
|---|---|
| Bromo derivative used: | 3-bromobenzonitrile |
| Yield: | 95% of the theoretical |
| Mass spectrum: | MH$^+$ 210 (100) |

2.11 2-Hydroxy-5-amino-2'-ethylbiphenyl Hydrochloride

| | |
|---|---|
| Bromo derivative used: | 1-bromo-2-ethylbenzene |
| Yield: | 95% of the theoretical |
| Mass spectrum: | MH$^+$ 213 (100) |

2.12 2-Hydroxy-5-amino-4'-ethylbiphenyl Hydrochloride

| | |
|---|---|
| Bromo derivative used: | 1-bromo-4-ethylbenzene |
| Yield: | 80% of the theoretical |
| Mass spectrum: | MH$^+$ 213 (100) |

2.13 2-Hydroxy-5-amino-2',4'-dimethylbiphenyl Hydrochloride

| | |
|---|---|
| Bromo derivative used: | 6-bromo-m-xylene |
| Yield: | 95% of the theoretical |
| Mass spectrum: | MH$^+$ 213 (100) |

2.14 2-Hydroxy-5-amino-2',3'-dimethylbiphenyl Hydrochloride

| | |
|---|---|
| Bromo derivative used: | 6-bromo-o-xylene |
| Yield: | 95% of the theoretical |
| Mass spectrum: | MH$^+$ 213 (100) |

2.15 2-Hydroxy-5-amino-2',5'-dimethylbiphenyl Hydrochloride

| | |
|---|---|
| Bromo derivative used: | 2-bromo-p-xylene |
| Yield: | 95% of the theoretical |
| Mass spectrum: | MH$^+$ 213 (100) |

2.16 2-Hydroxy-5-amino-3',5'-dimethylbiphenyl Hydrochloride

| | |
|---|---|
| Bromo derivative used: | 5-bromo-m-xylene |
| Yield: | 95% of the theoretical |
| Mass spectrum: | MH$^+$ 213 (100) |

2.17 2-Hydroxy-5-amino-3'aminomethylbiphenyl Hydrochloride

| | |
|---|---|
| Bromo derivative used: | 3-bromobenzylamine |
| Yield: | 87% of the theoretical |
| Mass spectrum: | MH$^+$ 251 (100) |

2.18 2-Hydroxy-5-amino-4'-methoxylbiphenyl Hydrochloride

| | |
|---|---|
| Bromo derivative used: | 4-bromoanisole |
| Yield: | 99% of the theoretical |
| Mass spectrum: | MH$^+$ 215 (100) |

2.19 2-Hydroxy-5-amino-2'-methoxylbiphenyl Hydrochloride

| | |
|---|---|
| Bromo derivative used: | 2-bromoanisole |
| Yield: | 79% of the theoretical |
| Mass spectrum: | MH$^+$ 215 (100) |

2.20 2-Hydroxy-5-amino-3'-methoxylbiphenyl Hydrochloride

| | |
|---|---|
| Bromo derivative used: | 3-bromoanisole |
| Yield: | 97% of the theoretical |
| Mass spectrum: | MH$^+$ 215 (100) |

2.21 2-Hydroxy-5-amino-5'-fluoro-2'-methylbiphenyl Hydrochloride

| | |
|---|---|
| Bromo derivative used: | 2-bromo-4-fluorotoluene |
| Yield: | 82% of the theoretical |
| Mass spectrum: | MH$^+$ 217 (100) |

2.22 4-Amino-2-(1H-indol-5-yl)phenol Hydrochloride

| | |
|---|---|
| Bromo derivative used: | 3-bromoindole |
| Yield: | 95% of the theoretical |
| Mass spectrum: | MH$^+$ 224 (100) |

2.23 1-(5'-Amino-2'-hydroxybiphenyl-3-yl)ethanone Hydrochloride

| | |
|---|---|
| Bromo derivative used: | 2-bromoacetophenone |
| Yield: | 56% of the theoretical |
| Mass spectrum: | MH$^+$ 227 (100) |

2.24 4-Amino-2-benzo[1,3]dioxol-5-ylphenol Hydrochloride

| | |
|---|---|
| Bromo derivative used: | 4-bromo-1,2-methylenedioxybenzene |
| Yield: | 93% of the theoretical |
| Mass spectrum: | MH$^+$ 229 (100) |

2.25 2-Hydroxy-5-amino-3'-ethoxybiphenyl Hydrochloride

| | |
|---|---|
| Bromo derivative used: | 1-bromo-3-ethoxybenzene |
| Yield: | 78% of the theoretical |
| Mass spectrum: | MH$^+$ 229 (100) |

2.26 2-Hydroxy-5-amino-4'-methoxy-2'-methylbiphenyl Hydrochloride

| | |
|---|---|
| Bromo derivative used: | 2-bromo-5-methoxytoluene |
| Yield: | 93% of the theoretical |
| Mass spectrum: | MH$^+$ 229 (100) |

2.27 2-Hydroxy-5-amino-2'-(2-hydroxyethyl)lbiphenyl Hydrochloride

| | |
|---|---|
| Bromo derivative used: | 2-(2-bromophenyl)ethanol |
| Yield: | 78% of the theoretical |
| Mass spectrum: | MH$^+$ 229 (100) |

2.28 2-Hydroxy-5-amino-4'-nitrobiphenyl Hydrochloride

| | |
|---|---|
| Bromo derivative used: | 4-bromonitrobenzene |
| Yield: | 93% of the theoretical |
| Mass spectrum: | MH$^+$ 230 (100) |

2.29 2-Hydroxy-5-amino-4'-methylsulfanylbiphenyl Hydrochloride

| | |
|---|---|
| Bromo derivative used: | 1-bromo-4-methylmercaptobenzene |
| Yield: | 93% of the theoretical |
| Mass spectrum: | MH$^+$ 231 (100) |

2.30 2-Hydroxy-5-amino-4'-tert.butylbiphenyl Hydrochloride

| | |
|---|---|
| Bromo derivative used: | 1-bromo-4-tert.butylbenzene |
| Yield: | 89% of the theoretical |
| Mass spectrum: | MH$^+$ 241 (100) |

2.31 2-Hydroxy-5-amino-2',4'-dimethoxybiphenyl Hydrochloride

| | |
|---|---|
| Bromo derivative used: | 6-bromo-1,3-dimethoxybenzene |
| Yield: | 88% of the theoretical |
| Mass spectrum: | MH$^+$ 245 (100) |

2.32 2-Hydroxy-5-amino-2',5'-dimethoxybiphenyl Hydrochloride

| | |
|---|---|
| Bromo derivative used: | 2-bromo-2,5-dimethoxybenzene |
| Yield: | 88% of the theoretical |
| Mass spectrum: | MH$^+$ 245 (100) |

2.33 2-Hydroxy-5-amino-4'-(2-hydroxyethoxy)biphenyl Hydrochloride

| | |
|---|---|
| Bromo derivative used: | 1-bromo-4-(2-hydroxyethoxy)benzene |
| Yield: | 88% of the theoretical |
| Mass spectrum: | MH$^+$ 245 (100) |

2.34 2-Hydroxy-5-amino-4'-trifluoromethylbiphenyl Hydrochloride

| | |
|---|---|
| Bromo derivative used: | 1-bromo-4-trifluoromethylbenzene |
| Yield: | 86% of the theoretical |
| Mass spectrum: | MH$^+$ 253 (100) |

2.35 2-Hydroxy-5-amino-3',4'-dimethylbiphenyl Hydrochloride

| | |
|---|---|
| Bromo derivative used: | 4-bromo-o-xylene |
| Yield: | 95% of the theoretical |
| Mass spectrum: | MH$^+$ 213 (100) |

2.36 2-Hydroxy-5-amino-4'-ethoxybiphenyl Hydrochloride

| | |
|---|---|
| Bromo derivative used: | 1-bromo-4-ethoxybenzene |
| Yield: | 93% of the theoretical |
| Mass spectrum: | MH$^+$ 229 (100) |

2.37 2-Hydroxy-5-amino-2'-methylsulfanylbiphenyl Hydrochloride

| | |
|---|---|
| Bromo derivative used: | 1-bromo-2-methylmercaptobenzene |
| Yield: | 93% of the theoretical |
| Mass spectrum: | MH$^+$ 231 (100) |

2.38 2-Hydroxy-5-amino-3'-fluorobiphenyl Hydrochloride

| | |
|---|---|
| Bromo derivative used: | 1-bromo-3-fluorobenzene |
| Yield: | 95% of the theoretical |
| Mass spectrum: | MH$^+$ 203 (100) |

2.39 5-Amino-2'-methylbiphenyl-2,4-'diol Hydrochloride

| | |
|---|---|
| Bromo derivative used: | 4-bromo-3-methylphenol |
| Yield: | 94% of the theoretical |
| Mass spectrum: | MH$^+$ 215 (100) |

2.40 2-Hydroxy-5-amino-4'-(2-hydroxyethyl)biphenyl Hydrochloride

| | |
|---|---|
| Bromo derivative used: | 1-bromo-4-(2-hydroxyethyl)benzene |
| Yield: | 75% of the theoretical |
| Mass spectrum: | MH$^+$ 229 (100) |

2.41 2-Hydroxy-5-amino-4'-(1-hydroxyethyl)biphenyl Hydrochloride

| | |
|---|---|
| Bromo derivative used: | 1-bromo-4-(1-hydroxyethyl)benzene |
| Yield: | 56% of the theoretical |
| Mass spectrum: | MH$^+$ 229 (100) |

Examples 3 to 44

Hair Colorants

Hair colorant solutions having the following composition were prepared:

| | | |
|---|---|---|
| 1.25 | mmoles | of developer of formula (I) according to Table 1 |
| 1.25 | mmoles | of coupler according to Table 1 |
| 1.0 | g | of potassium oleate (8% aqueous solution) |
| 1.0 | g | of ammonia (22% aqueous solution) |
| 1.0 | g | of ethanol |
| 0.3 | g | of ascorbic acid |
| to 100.0 | g | water |

Immediately before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Coupler | | | |
|---|---|---|---|---|---|
| Example | Developer of Formula (I) | I. 1,3-Dihydroxybenzene | II. 1,3-Diamino-4-(2-hydroxyethoxy benzene sulfate | III. 5-Amino-2-methylphenol | IV. 1-Naphthol |
| 3 | 1D | light-blond | red-violet | red-orange | violet |
| 4 | 2.1 | light-blond | red-violet | red-orange | violet |
| 5 | 2.2 | light-blond | light-violet | light-orange | light-violet |
| 6 | 2.3 | light-blond | light-violet | light-orange | light-violet |
| 7 | 2.4 | light-blond | light-violet | light-orange | light-violet |
| 8 | 2.5 | light-blond | light-violet | light-orange | light-violet |
| 9 | 2.6 | light-blond | light-violet | light-orange | light-violet |
| 10 | 2.7 | light-blond | light-violet | light-orange | light-violet |
| 11 | 2.8 | light-blond | light-violet | light-orange | light-violet |
| 12 | 2.9 | light-blond | light-violet | light-orange | light-violet |
| 13 | 2.10 | light-blond | light-violet | light-orange | light-violet |
| 14 | 2.11 | light-blond | light-violet | light-orange | light-violet |
| 15 | 2.12 | light-blond | light-violet | light-orange | light-violet |
| 16 | 2.13 | light-blond | light-violet | light-orange | light-violet |
| 17 | 2.14 | light-blond | light-violet | light-orange | light-violet |
| 18 | 2.15 | light-blond | light-violet | light-orange | light-violet |
| 19 | 2.16 | light-blond | light-violet | light-orange | light-violet |
| 20 | 2.17 | light-blond | light-violet | light-orange | light-violet |
| 21 | 2.18 | light-blond | light-violet | light-orange | light-violet |
| 22 | 2.19 | light-blond | light-violet | light-orange | light-violet |
| 23 | 2.20 | light-blond | light-violet | light-orange | light-violet |
| 24 | 2.21 | light-blond | light-violet | light-orange | light-violet |
| 25 | 2.22 | light-blond | light-violet | light-orange | light-violet |
| 26 | 2.23 | light-blond | light-violet | light-orange | light-violet |
| 27 | 2.24 | light-blond | light-violet | light-orange | light-violet |
| 28 | 2.25 | light-blond | light-violet | light-orange | light-violet |
| 29 | 2.26 | light-blond | light-violet | light-orange | light-violet |
| 30 | 2.27 | light-blond | light-violet | light-orange | light-violet |
| 31 | 2.28 | light-blond | light-violet | light-orange | light-violet |
| 32 | 2.29 | light-blond | light-violet | light-orange | light-violet |
| 33 | 2.30 | light-blond | light-violet | light-orange | light-violet |
| 34 | 2.31 | light-blond | light-violet | light-orange | light-violet |
| 35 | 2.32 | light-blond | light-violet | light-orange | light-violet |
| 36 | 2.33 | light-blond | light-violet | light-orange | light-violet |
| 37 | 2.34 | light-blond | light-violet | light-orange | light-violet |
| 38 | 2.35 | light-blond | light-violet | light-orange | light-violet |
| 39 | 2.36 | light-blond | light-violet | light-orange | light-violet |
| 40 | 2.37 | light-blond | light-violet | light-orange | light-violet |
| 41 | 2.38 | light-blond | light-violet | light-orange | light-violet |
| 42 | 2.39 | light-blond | light-violet | light-orange | light-violet |
| 43 | 2.40 | light-blond | light-violet | light-orange | light-violet |
| 44 | 2.41 | light-blond | light-violet | light-orange | light-violet |

Examples 45 to 60

Hair Colorants

Hair colorant solutions having the following composition were prepared:

| | | |
|---|---|---|
| X g | of developer E1 of formula (I) according to Table 2 |
| U g | of developer E2 to E9 according to Table 2 |
| Y g | of coupler K11 to K36 according to Table 4 |
| Z g | of direct dye D1 to D3 according to Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Immediately before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. The coloring results are presented in Table 5.

Examples 61 to 66

Hair Colorants

Dye carriers in cream form and having the following composition were prepared:

| | |
|---|---|
| X g | of developer E1 of formula (I) according to Table 2 |
| Y g | of coupler K11 to K36 according to Table 4 |
| Z g | of direct dye D2 according to Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Immediately before use, 40 g of the foregoing coloring cream was mixed with 40 g of a 6% aqueous solution of hydrogen peroxide. The mixture was then applied to the hair. After an exposure time of 30 min, the hair was rinsed with water, washed with a commercial shampoo and dried. The coloring results are presented in the following Table 6.

TABLE 2

Developers

| | |
|---|---|
| E1 | 2-hydroxy-5-aminobiphenyl hydrochloride (according to Example 1D) |
| E2 | 1,4-Diaminobenzene |
| E3 | 2,5-Diaminophenylethanol sulfate |
| E4 | 3-Methyl-4-aminophenol |
| E5 | 4-Amino-2-aminomethylphenol dihydrochloride |
| E6 | 4-Aminophenol |
| E7 | N,N,-Bis-(2'-hydroxyethyl)-p-phenylenediamine sulfate |
| E8 | 4,5-Diamino-1-(2'-hydroxyethyl)pyrazole sulfate |
| E9 | 2,5-Diaminotoluene sulfate |

TABLE 3

Direct Dyes

| | |
|---|---|
| D1 | 2,6-Diamino-3-[(pyridin-3-yl)azo]pyridine |
| D2 | 6-Chloro-2-ethylamino-4-nitrophenol |
| D3 | 2-Amino-6-chloro-4-nitrophenol |

TABLE 4

Couplers

| | |
|---|---|
| K11 | 1,3-Diaminobenzene |
| K12 | 2-Amino-4-(2'-hydroxyethyl)aminoanisole sulfate |
| K13 | 1,3-Diamino-4-(2'-hydroxyethoxy)benzene sulfate |
| K14 | 2,4-Diamino-5-fluorotoluene sulfate |
| K15 | 3-Amino-2-methylamino-6-methoxypyridine |
| K16 | 3,5-Diamino-2,6-dimethoxypyridine dihydrochloride |
| K17 | 2,4-Diamino-5-ethoxytoluene sulfate |
| K18 | N-(3-Dimethylamino)phenylurea |
| K19 | 1,3-Bis-(2,4-diaminophenoxy)propane tetrahydrochloride |
| K21 | 3-Aminophenol |
| K22 | 5-Amino-2-methylphenol |
| K23 | 3-Amino-2-chloro-6-methylphenol |
| K24 | 5-Amino-4-fluoro-2-methylphenol sulfate |
| K25 | 1-Naphthol |
| K26 | 1-Acetoxy-2-methylnaphthalene |
| K31 | 1,3-Dihydroxybenzene |
| K32 | 2-Methyl-1,3-dihydroxybenzene |
| K33 | 1-Chloro-2,4-dihydroxybenzene |
| K34 | 4-(2'-Hydroxyethyl)amino-1,2-methylenedioxybenzene hydrochloride |
| K35 | 3,4-Methylenedioxyphenol |
| K36 | 2-Amino-5-methylphenol |

TABLE 5

Hair Colorants

| | Example | | | | | |
|---|---|---|---|---|---|---|
| | 45 | 46 | 47 | 48 | 49 | 50 |
| Dye | (Quantity of dye in grams) | | | | | |
| E1 | 0.096 | 0.24 | 0.3 | 0.04 | 0.01 | 0.7 |
| E2 | — | — | — | 0.9 | — | — |
| E5 | — | — | — | — | — | — |
| E6 | — | — | — | — | — | — |
| E9 | — | — | — | — | 0.096 | 1.8 |
| K12 | — | — | — | — | 0.01 | — |
| K18 | — | — | — | — | — | 0.03 |
| K21 | — | — | — | — | 0.02 | 0.06 |
| K22 | 0.08 | 0.2 | 0.25 | 0.056 | — | 0.58 |
| K25 | — | — | — | — | 0.03 | — |
| K31 | — | — | — | 0.2 | — | 0.8 |
| K32 | — | 0.03 | 0.05 | 0.316 | — | — |
| K35 | 0.018 | — | — | — | — | — |
| K36 | — | 0.03 | 0.05 | 0.01 | — | — |
| K26 | | | | | | |
| D1 | — | — | — | 0.01 | — | — |
| D3 | 0.04 | 0.06 | 0.025 | — | — | — |
| Shade | light-blond copper gold | copper gold | bright purple | purple-brown | silver-blond | dark mahogany |

| | Example | | | | | |
|---|---|---|---|---|---|---|
| | 51 | 52 | 53 | 54 | 55 | 56 |
| Dye | (Quantity of dye in grams) | | | | | |
| E1 | 0.01 | 0.6 | 1 | 0.2 | 0.8 | 0.6 |
| E2 | 2.0 | — | — | 1.9 | — | — |
| E3 | — | 0.05 | — | — | — | — |
| E8 | — | — | 1 | — | — | — |
| E9 | — | — | — | — | 1.0 | 0.7 |

TABLE 5-continued

| Dye | | | | | | |
|---|---|---|---|---|---|---|
| K12 | — | — | 1.1 | — | — | — |
| K13 | 0.07 | — | — | — | — | 0.8 |
| K16 | — | — | — | — | — | 1.0 |
| K17 | — | — | 1.1 | — | — | — |
| K18 | — | — | — | 1.25 | — | — |
| K21 | 0.4 | — | — | 0.28 | — | — |
| K22 | 0.08 | 0.5 | — | — | — | — |
| K25 | — | — | — | — | 0.8 | — |
| K31 | 0.8 | — | — | — | — | — |
| K32 | — | 0.03 | — | — | — | — |
| K33 | — | — | — | — | 0.75 | — |
| K36 | — | 0.03 | — | — | — | — |
| D1 | — | 0.25 | — | — | — | — |
| D3 | — | 0.15 | — | — | — | — |
| Shade | black-brown | orange | blue-violet | blue-red | pink | Bordeaux red |

| | Example | | | |
|---|---|---|---|---|
| Dye | 57 | 58 | 59 | 60 |
| | (Quantity of dye in grams) | | | |
| E1 | 0.01 | 0.01 | 0.05 | 0.6 |
| E3 | 1.4 | 4.5 | — | — |
| E5 | — | — | — | 0.25 |
| E6 | — | — | 0.1 | — |
| E8 | — | 0.8 | 0.5 | 0.01 |
| E9 | 2.5 | — | — | — |
| K12 | 0.6 | — | — | — |
| K13 | 0.2 | — | — | 0.8 |
| K14 | — | 0.25 | — | — |
| K16 | 0.01 | — | — | — |
| K18 | — | — | — | 1.25 |
| K19 | 0.8 | — | — | — |
| K21 | 0.3 | — | — | 0.28 |
| K22 | — | 5.0 | — | — |
| K25 | — | 0.4 | — | — |
| K23 | — | — | 0.6 | — |
| K31 | 1.1 | — | — | — |
| K32 | — | — | — | 0.33 |
| K36 | — | — | 0.19 | — |
| D2 | — | — | 0.5 | — |
| Shade | black | red-violet | red-orange | warm yellow |

TABLE 6

Hair Colorants

| | Example | | | | | |
|---|---|---|---|---|---|---|
| Dye | 61 | 62 | 63 | 64 | 65 | 66 |
| | (Quantity of dye in grams) | | | | | |
| E1 | 0.1 | 0.2 | 0.01 | 2.0 | 0.5 | 0.7 |
| E4 | — | — | — | — | — | 1.6 |
| E8 | — | — | — | 0.25 | 0.8 | 0.2 |
| E9 | 3.2 | 1.71 | 0.02 | — | — | 1.8 |
| K13 | 0.23 | 0.1 | — | — | 1.3 | — |
| K14 | 0.2 | — | — | — | — | — |
| K16 | — | — | 0.015 | — | — | — |
| K21 | 0.4 | 0.8 | — | — | 0.02 | — |
| K22 | 0.08 | — | 0.25 | 1.8 | — | 4.5 |
| K23 | — | 0.2 | — | — | 0.03 | — |
| K31 | 1.05 | 0.135 | 0.02 | 0.25 | — | 0.08 |
| K25 | — | — | — | — | — | 0.55 |
| K26 | — | — | 0.03 | — | — | — |
| K19 | — | — | — | — | 1.7 | — |
| K36 | — | 0.27 | — | — | — | — |
| D2 | — | 0.01 | — | — | — | — |
| Shade | dark-brown | chocolate brown | silver-blond | orange | blue-violet | red violet |

Unless otherwise indicated, all percentages given in the present application are by weight.

What is claimed is:

1. A colorant for oxidative dyeing of keratin fibers, particularly human hair, based on a developer-coupler combination, said colorant containing, as developer, at least one 2-hydroxy-5-aminobiphenyl derivative compound of formula (I), or a physiologically tolerated, water-soluble salt thereof:

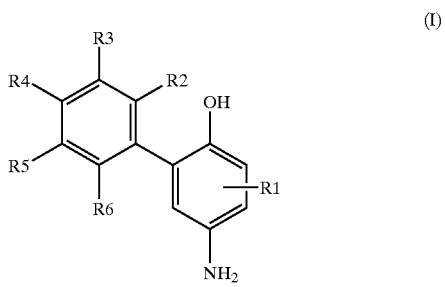

(I)

wherein R1 denotes hydrogen, a halogen atom, a $C_1$–$C_4$-alkyl group, a $C_1$–$C_4$-hydroxyalkyl group, a $C_1$–$C_4$-alkoxy group or a $C_1$–$C_4$-hydroxyalkoxy group;

wherein R2, R3, R4, R5, R6 can be equal or different and, independently of each other, denote hydrogen, a halogen atom, a cyano group, a hydroxy group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a dialkylamino group, a trifluoromethyl group, a —C(O)H group, a —C(O)CH$_3$ group, a —C(O)CF$_3$ group, an —SI(CH$_3$)$_3$ group, a $C_1$–$C_4$-hydroxyalkyl group, a $C_3$–$C_4$-dihydroxyalkyl group, a —CH=CHR7 group, a —(CH$_2$)$_p$—CO$_2$R8 group or a —(CH$_2$)$_p$—R9 with p=1,2,3 or 4, a —C(R10)=NR11 or C(R12)H—NR13R14 group, or two adjacent R2 to R6 groups form an —O—CH$_2$—O— bridge;

R7 denotes hydrogen, a hydroxy group, a nitro group, an amine group, a —CO$_2$R12 group or a —C(O)CH$_3$ group;

R8, R10 and R13 can be equal or different and, independently of each other, denote hydrogen or a $C_1$–$C_4$-alkyl group;

R9 denotes an amino group or a nitrile group,

R11, R14 and R15 can be equal or different and, independently of each other, denote hydrogen, a hydroxy group, a $C_1$–$C_4$-alkyl group, a $C_1$–$C_4$-hydroxyalkyl group, a $C_3$–$C_4$-dihydroxyalkyl group or a radical of formula

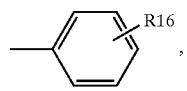

R12 denotes hydrogen, an amino group or a hydroxy group, and provided that the at least one 2-hydroxy-5-aminobiphenyl derivative compound of the formula (I) does not have a center of symmetry and that, it one of R3 and R6 denotes an amino group, an alkylamino group or a dialkylamino group, another of R3 and R6 different from said one of R3 and R6 does not denote an amino group, an alkylamino group or a dialkylamino group.

2. The colorant according to claim 1, wherein R1 denotes hydrogen.

3. A colorant for oxidative dyeing of keratin fibers, particularly human hair, based on a developer-coupler combination, said colorant containing, as developer, at least one 2-hydroxy-5-aminobiphenyl derivative compound of formula (I), or a physiologically tolerated, water-soluble salt thereof:

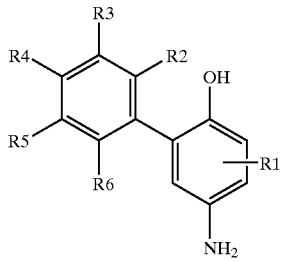
(I)

wherein R1 denotes hydrogen;

wherein R2, R3, R4, R5, R6 can be equal or different and, independently of each other, denote hydrogen, a halogen atom, a cyano group, a hydroxy group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a dialkylamino group, a trifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group, a $C_3$–$C_4$-dihydroxyalkyl group, a —CH=CHR7 group, a —(CH$_2$)$_p$—CO$_2$R8 group or a —(CH$_2$)$_p$—R9 with p=1,2,3 or 4, a —C(R10)=NR11 or C(R12)H—NR13R14 group, or two adjacent R2 to R6 groups form an —O—CH$_2$—O— bridge;

R7 denotes hydrogen, a hydroxy group, a nitro group, an amino group, a —CO$_2$R12 group or a —C(C)CH$_3$ group;

R8, R10 and R13 can be equal or different and, independently of each other, denote hydrogen or a $C_1$–$C_4$-alkyl group;

R9 denotes an amino group or a nitrile group;

R11, R14 and R15 can be equal or different and, independently of each other, denote hydrogen, a hydroxy group, a $C_1$–$C_4$-alkyl group, a $C_1$–$C_4$-hydroxyalkyl group, a $C_3$–$C_4$-dihydroxyalkyl group or a radical of formula

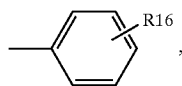,

R12 denotes hydrogen, an amino group or a hydroxy group; and wherein four of R2, R3, R4, R5 and R6 each denote hydrogen while a remaining fifth of R2, R3, R4, R5 and R6 is selected from the group consisting of hydrogen, a methyl group, an amino group, a hydroxy group, a methoxy group, $C_1$–$C_4$-hydroxyalkyl groups and $C_1$–$C_4$-hydroxyalkoxy groups; and provided that the at least one 2-hydroxy-5-aminobiphenyl derivative compound of the formula (I) does not have a center of symmetry.

4. A colorant for oxidative dyeing of keratin fibers, particularly human hair, based on a developer-coupler combination, said colorant containing, as developer, at least one 2-hydroxy-5-aminobiphenyl derivative compound of formula (I), or a physiologically tolerated, water-soluble salt thereof;

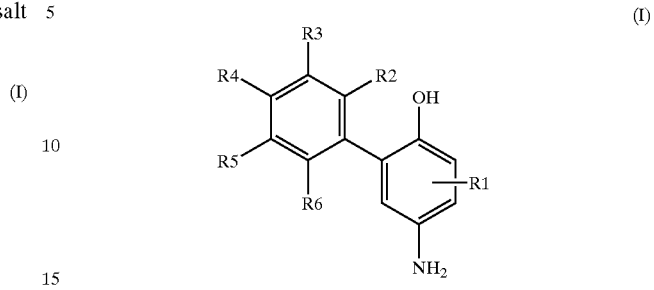

wherein R1, R2, R3, R4, R5 and R6 each denote hydrogen.

5. A colorant for oxidative dyeing of keratin fibers, particularly human hair, based on a developer-coupler combination, said colorant containing, as developer, at least one 2-hydroxy-5-aminobiphenyl derivative compound of formula (I), or a physiologically tolerated, water-soluble salt thereof:

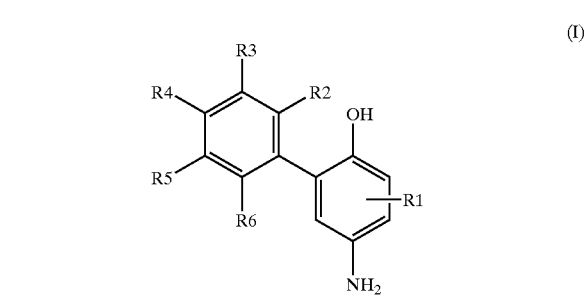

wherein R1 denotes hydrogen, a halogen atom, a $C_1$–$C_4$-alkyl group, a $C_1$–$C_4$-hydroxyalkyl group, a $C_1$–$C_4$-alkoxy group or a $C_1$–$C_4$-hydroxyalkoxy group;

wherein R2, R3, R4, R5, R6 can be equal or different and, independently of each other, denote hydrogen, a halogen atom, a cyano group, a hydroxy group, a $C_1$–$C_4$-alkoxy group, a $C_1$–$C_4$-hydroxyalkoxy group, a $C_1$–$C_4$-alkyl group, a $C_1$–$C_4$-alkyl thioether group, a mercapto group, a nitro group, an amino group, an alkylamino group, a dialkylamino group, a bifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group, a $C_3$–$C_4$-dihydroxyalkyl group, a —CH=CHR7 group, a —(CH$_2$)$_p$—CO$_2$R8 group or a —(CH$_2$)$_p$—R9 with p=1,2,3 or 4, a —C(R10)=NR11 or C(R12)H—NR13R14 group, or two adjacent R2 to R6 groups form an —O—CH$_2$—O— bridge;

R7 denotes hydrogen, a hydroxy group, a nitro group, an amino group, a —CO$_2$R12 group or a —C(O)CH$_3$ group;

R8, R10 and R13 can be equal or different and, independently of each other, denote hydrogen or a $C_1$–$C_4$-alkyl group;

R9 denotes an amino group or a nitrite group;

R11, R14 and R15 can be equal or different and, independently of each other, denote hydrogen, a hydroxy group, a $C_1$–$C_4$-alkyl group, a $C_1$–$C_4$-hydroxyalkyl group, a $C_3$–$C_4$-dihydroxyalkyl group or a radical of formula

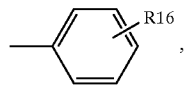

R12 denotes hydrogen, an amino group or a hydroxy group; and wherein four of R2, R3, R4, R5 and R6 each denote hydrogen while a remaining fifth is selected from the group consisting of hydrogen, a methyl group, an amino group, a hydroxy group, a methoxy group, $C_1$–$C_4$-hydroxyalkyl groups and $C_1$–$C_4$-hydroxyalkoxy groups; and provided that the at least one 2-hydroxy-5-aminobiphenyl derivative compound of the formula (I) does not have a center of symmetry.

6. A colorant for oxidative dyeing of keratin fibers, particularly human hair, based on a developer-coupler combination, said colorant containing, as developer, at least one 2-hydroxy-5-aminobiphenyl derivative selected from the group consisting of 2-hydroxy-5-aminobiphenyl, 2,4'-dihydroxy-5-aminobiphenyl, 2-hydroxy-5-amino-4'-(2"-hydroxyethoxy)biphenyl 2,4'-dihydroxy-5-amino-2'-methylbiphenyl, 2-hydroxy-5-amino-4'-(2"-hydroxyethyl)biphenyl and 2-hydroxy-5,4'-diaminobiphenyl;

or a physiologically tolerated, water-soluble salt thereof.

7. The colorant according to claim 1, containing from about 0.005 to 20.0 wt. % of said at least one 2-hydroxy-5-aminobiphenyl derivative compound of the formula (I).

8. The colorant according to claim 1, having a pH of 6.5 to 11.5.

9. A 2-hydroxy-5-aminobiphenyl derivative compound of formula (Ia), or a physiologically tolerated, water-soluble salt thereof:

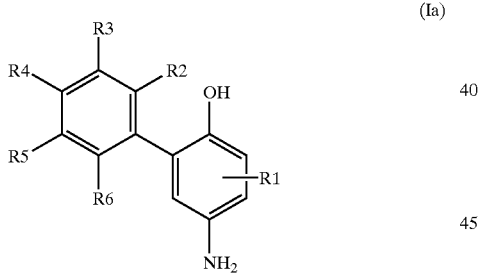

(Ia)

wherein R1 denotes hydrogen, a halogen atom, a $C_1$–$C_4$-alkyl group, a $C_1$–$C_4$-hydroxy-alkyl group, a $C_1$–$C_4$-alkoxy group or a $C_1$–$C_4$-hydroxyalkoxy group;

R2, R3, R4, R5, R6 can be equal or different and independently of each other denote hydrogen, a halogen atom, a cyano group, a hydroxy group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, an alkylamino group, a dialkylamino group, a trifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group, a $C_3$–$C_4$-dihydroxyalkyl group, a —CH=CHR7 group, a —(CH$_2$)$_p$—CO$_2$R8 group or a —(CH$_2$)$_p$—R9 with p=1,2,3 or 4, a —C(R10)=NR11 or C(R12)H—NR13R14 group, or two adjacent R2 to R6 groups form an —O—CH$_2$—O— bridge;

R7 denotes hydrogen, a hydroxy group, a nitro group, an amino group, a —CO$_2$R12 group or a —C(O)CH$_3$ group;

R8, R10 and R13 can be equal or different and, independently of each other, denote hydrogen or a $C_1$–$C_4$-alkyl group;

R9 denotes an amino group or a nitrile group;

R11, R14 and R15 can be equal or different and, independently of each other, denote hydrogen, a hydroxy group, a $C_1$–$C_4$-alkyl group, a $C_1$–$C_4$-hydroxyalkyl group, a $C_3$–$C_4$-dihydroxyalkyl group or a radical of formula

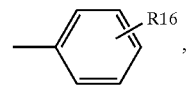

R12 denotes hydrogen, an amino group or a hydroxy group; and with the proviso that (I) the compound of formula (Ia) does not have a center of symmetry; that (ii) R2 does not denote hydrogen or a hydroxy group;

that (iii) if one of R3 and R6 denotes an amino group, an alkylamino group or a dialkylamino group, another of R3 and R6 different from said one of R3 and R6 does not denote an amino group, an alkylamino group or a dialkylamino group;

and that (iv) if R1 and three of the R2, R3, R4, R5 and R6 each denote hydrogen, and one of the remaining R2, R3, R4, R5 and R6 denotes hydrogen, a halogen atom or a $C_1$- to $C_6$-alkyl group, another of the remaining R2, R3, R4, R5 and R6 does not denote a halogen atom, a cyano group, a hydroxy group, a $C_1$–$C_4$-alkoxy group, a $C_1$–$C_4$-alkylthioether group, a nitro group, an amino group, an alkyl amino group, a dialkylamino group or a trifluoromethyl group.

* * * * *